United States Patent [19]
Chow

[11] Patent Number: 5,300,499
[45] Date of Patent: Apr. 5, 1994

[54] 5-SUBSTITUTED 3-THIOPHENE SULFONAMIDES AS ANTIGLAUCOMA AGENTS

[75] Inventor: Ken Chow, Irvine, Calif.

[73] Assignee: Allergan, Inc., Irvine, Calif.

[21] Appl. No.: 939,189

[22] Filed: Sep. 2, 1992

[51] Int. Cl.$^5$ .............. A61K 31/38; C07D 333/32
[52] U.S. Cl. ..................... 514/231.5; 514/326; 514/336; 514/422; 514/444; 514/445; 544/146; 546/212; 546/213; 546/268; 546/284; 548/527; 549/59; 549/60; 549/64; 549/65
[58] Field of Search ............ 549/64, 59, 60, 65; 514/445, 444, 231.5, 326, 336, 422; 544/146; 546/212, 213, 268, 284; 548/527

[56] References Cited

U.S. PATENT DOCUMENTS

| | | | |
|---|---|---|---|
| 3,888,879 | 6/1975 | Edwards | 549/65 |
| 4,386,098 | 5/1983 | Woltersdorf, Jr. et al. | 424/470 |
| 4,416,890 | 11/1983 | Woltersdorf, Jr. | 548/166 |
| 4,426,388 | 1/1984 | Woltersdorf, Jr. | 548/166 |
| 4,477,466 | 10/1984 | Shephard | 546/208 |
| 4,486,444 | 12/1984 | Shepard | 514/445 |
| 4,542,152 | 9/1985 | Shephard | 514/445 |
| 4,544,667 | 10/1985 | Shephard et al. | 549/466 |
| 4,585,787 | 4/1986 | Shephard | 514/445 |
| 4,665,090 | 5/1987 | Grahm | 514/445 |
| 4,847,289 | 7/1989 | Baldwin | 514/444 |
| 4,914,111 | 4/1990 | Hartman et al. | 514/445 |
| 4,929,637 | 5/1990 | Baldwin et al. | 514/445 |

FOREIGN PATENT DOCUMENTS

| | | | |
|---|---|---|---|
| 268396 | 5/1988 | European Pat. Off. | 549/64 |
| 1059921 | 6/1959 | Fed. Rep. of Germany . | |
| 850982 | 10/1960 | United Kingdom . | |

Primary Examiner—Richard L. Raymond
Attorney, Agent, or Firm—Martin A. Voet; Robert J. Baran; James M. Hoch

[57] ABSTRACT

The present invention provides novel carbonic anhyrase inhibitors represented by the structural formula:

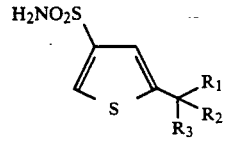

wherein $R_1$ and $R_2$ are, for example, independently
(a) hydrogen; or
(b) $OR_4$, wherein $R_4$ is hydrogen or $C_{1-7}$ alkyl; or
(c) $NR_5R_6$, wherein $R_5$ and $R_6$ are independently hydrogen, or $C_{1-7}$ alkyl, or $C_{1-7}$ alkyl substituted with one or more halogen or $OR_4$; or
(d) —$COR_7$, wherein $R_7$ is hydrogen, $C_{1-7}$ alkyl, or $NR_5R_6$; or
(e) —$SR_8$, wherein $R_8$ is hydrogen or $C_{1-7}$ alkyl, or $C_{1-7}$ alkyl substituted with one or more halogen, or $OR_4$; or
(f) $C_{1-7}$ alkyl, or $C_{1-7}$ alkyl substituted with one or more halogen, or $OR_4$ or $NR_5R_6$; or
(g) $R_1$ and $R_2$ are together
  (i) =O, or
  (ii) =$NOR_8$ or
  (iii) =S;

and $R_3$ is
(h) $C_{1-7}$ alkyl or $C_{1-7}$ substituted with one or more halogen, $OR_4$ or $NR_5R_6$.

40 Claims, No Drawings

5-SUBSTITUTED 3-THIOPHENE SULFONAMIDES AS ANTIGLAUCOMA AGENTS

BACKGROUND OF THE INVENTION

1. Field of the Invention

The present invention relates to thiophenesulfonamides that have carbonic anhydrase inhibition activity and are useful as anti-glaucoma agents.

2. Background of the Art

Glaucoma is an ocular disorder associated with elevated intraocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many $\beta$-adrenergic blocking agents are effective in reducing intraocular pressure. While many of these agents are effective in reducing intraocular pressure, they also have other characteristics, e.g. membrane stabilizing activity, that are not acceptable for chronic ocular use. (S)-1-tert-Butylamino-3-[(4-morpholino-1,2,5-thiadiazol-3-yl)oxy]-2-propanol, a $\beta$-adrenergic blocking agent, was found to reduce intraocular pressure and to be devoid of many unwanted side effects associated with pilocarpine and, in addition, to possess advantages over many other $\beta$-adrenergic blocking agents, e.g., to be devoid of local anesthetic properties, to have a long duration of activity, and to display minimal tolerance.

Although pilocarpine, physostigmine and the $\beta$-adrenergic blocking agents mentioned above reduce intraocular pressure, none of these drugs manifests its action by inhibiting the enzyme carbonic anhydrase and, thereby, impeding the contribution to aqueous humor formation made by the carbonic anhydrase pathway.

Agents referred to as carbonic anhydrase inhibitors, block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such a gross disruption of a basic enzyme system is justified only during an acute attack of alarmingly elevated intraocular pressure, or when no other agent is effective.

Topically effective carbonic anhydrase inhibitors are reported in U.S. Pat. Nos. 4,386,098; 4,416,890; and 4,426,388. The compounds reported therein are 5 (and 6)-hydroxy-2-benzothiazolesulfonamides and acyl esters thereof.

Additionally, U.S. Pat. No. 4,544,667 discloses a series of benzofuran-2-sulfonamides, and U.S. Pat. Nos. 4,477,466; 4,486,444; 4,542,152; and 4,585,787 disclose 5-phenylsulfonylthiophene-2-sulfonamides and 5-benzoylthiophene-2-sulfonamides and alkanoyloxy derivatives thereof which are reported to be topically effective carbonic anhydrose inhibitors useful in the treatment of elevated intraocular pressure and glaucoma.

Finally, U.S. Pat. No. 4,914,111 reports that thiophene or furan-2-sulfonamides, having a 4-benzyl substituent are effective for the topical treatment of elevated intraocular pressure and glaucoma.

In view of the above, it is clear that a great deal of research has been carried out on the use of sulfonamides for the topical treatment of glaucoma. Furthermore, certain thiophenesulfonamides have been suggested for the topical treatment of glaucoma. However, the use of 3-thiophenesulfonamides has not been suggested for use in the topical treatment of glaucoma.

Therefore, it is one objective of this invention to provide 3-thiophenesulfonamides for the treatment of glaucoma.

It is another object of this invention to provide compounds having carbonic anhydrase inhibition activity.

Another object of this invention is to provide a method of inhibiting carbonic anhydrase activity to thereby treat glaucoma.

Other objects and advantages of the instant invention will become apparent from a careful reading of the specification below.

SUMMARY OF THE INVENTION

The present invention provides novel compounds having carbonic anhydrase inhibition activity and useful in the treatment of glaucoma. These compounds are represented by the structural formula:

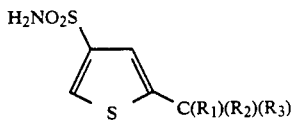

wherein $R_1$ and $R_2$ are independently
  (a) hydrogen; or
  (b) $OR_4$, wherein $R_4$ is hydrogen or $C_{1-7}$ alkyl or $C_{1-3}$ alkylcarbonyl or phenylcarbonyl or phenyl; or
  (c) $NR_5R_6$, wherein $R_5$ and $R_6$ are independently hydrogen, or $C_{1-7}$ alkyl, or $C_{1-7}$ alkyl substituted with one or more halogen or $OR_4$; or
  (d) $-COR_7$, wherein $R_7$ is hydrogen, $C_{1-7}$ alkyl, or $NR_5R_6$; or
  (e) $-SR_8$, wherein $R_8$ is hydrogen or $C_{1-7}$ alkyl, or $C_{1-7}$ alkyl substituted with one or more halogen, or $OR_4$; or
  (f) $C_{1-7}$ alkyl, or $C_{1-7}$ alkyl substituted with one or more halogen, or $OR_4$ or $NR_5R_6$; or
  (g) $R_1$ and $R_2$ are together
    (i) =O, or
    (ii) =NOR_8, or
    (iii) =S;
and $R_3$ is
  (h) $C_{1-7}$ alkyl or $C_{1-7}$ substituted with one or more halogen, $OR_4$ or $NR_5R_6$; or
  (i) aryl, wherein said aryl comprises up to 10 carbon atoms and is an unsubstituted carbocyclic aryl or heterocyclic aryl, which may be selected from the group consisting of phenyl, thienyl, furyl, pyridyl, pyrryl, piperidyl, pyrrolidyl, morpholinyl, or said carbocyclic aryl or heterocyclic aryl is substituted with one or more halogen, or $OR_4$, or $NR_5R_6$, or carboxylic acid or lower alkyl esters thereof, or carboxaldehyde or $C_{1-7}$ alkyl, or $C_{1-7}$ alkyl substituted with one or more halogen, or $OR_4$, or $NR_5R_6$ or carboxylic acid or lower alkyl esters thereof; or (j) $-COR_9$, wherein $R_9$ is $R_7$ or a carbocyclic or a heterocyclic radical, e.g. aryl, wherein said carbocyclic or a heterocyclic radical comprises up to 10 carbon atoms and may be selected from the group consisting of phenyl, cyclopentyl, cyclohexyl, thienyl, furyl, pyridyl, pyrryl, piperidyl, pyrrolidyl, morpholinyl or said carbocyclic aryl or heterocyclic aryl radical is substituted with one or more halogen, or $OR_4$, or $NR_5R_6$, or $C_{1-7}$ or $C_{1-7}$ alkyl substituted with one or more halogen, $OR_4$ or $NR_5R_6$.

Preferably, in the novel compounds of the invention $R_1$ and $R_2$, together, represent O; or at least one of $R_1$ or $R_2$ is hydrogen and the other is OH, $OCOCH_3$, NOH, or H. (That is, the novel compounds of this invention may include an alpha carbonyl or hydroxy, or acetoxy, or hydroxyamino, etc. group at the 5 position on the thiophene ring.) $R_3$ preferably represents $C_1$ to $C_6$ alkyl or phenyl or phenyl substituted with one or more, more preferably one, hydroxy, methoxy, acetoxy, acetoxymethylene, carboxy, hydroxymethyl, formyl, N,N-dimethylaminomethyl fluoro, chloro or bromo radicals.

DETAILED DESCRIPTION OF THE INVENTION

The novel compounds of the invention may be prepared by the following general reaction scheme:

4-Bromo-2-thiophenecarboxaldehyde is reacted with $R_3Li$ or $R_3MgX$, wherein X is a halogen, e.g., bromo or iodo, in tetrahydrofuran, or any other dipolar, aprotic solvent, e.g. diethylether, dioxane, etc., at a temperature of from about 0° C. to −78° C., to yield an alkoxide of the addition product. This intermediate is reacted with trimethylsilylchloride, at a temperature of from about 0° C. to −78° C., to provide a "protected" alcohol. The protected intermediate is consecutively reacted with n-Butyllithium in tetrahydrofuran at a temperature of about −100° C. to yield the 3-lithio compound. The lithio compound is reacted with $SO_2$ at a temperature of about −100° C. in THF, or other aprotic solvent, to yield the lithio sulfinate. The lithium sulfinate is reacted with N-chloro succinimide (NCS) at ambient temperatures in dichloromethane to yield the sulfonyl chloride. The sulfonyl chloride is consecutively reacted with $NH_4OH$ and tetra-n-butyl ammonium fluoride to yield a novel compound of the invention represented by the general formula:

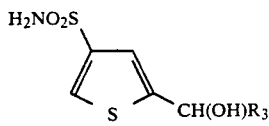

I

I may be oxidized by Jones' reagent to yield a novel compound of the invention represented by the general formula:

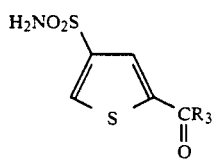

II

That is, II represents the alpha carbonyl derivatives of the invention, i.e., wherein $R_1$ and $R_2$ together, represent O (oxygen).

II may be reacted with $H_2NOH \cdot HCl$ in pyridine to provide compounds of the invention represented by the general formula:

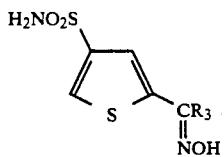

III

That is, in the compounds represented by Formula III, $R_1$ and $R_2$, together, represent NOH.

Alternatively, compounds represented by Formula I may be reacted with acetic anhydride in pyridine to yield compounds of the invention represented by the general formula:

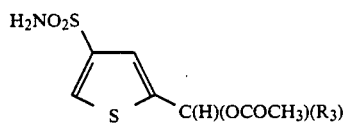

IV

That is, in the compounds represented by Formula IV, $R_1$ represents $OCOCH_3$ and $R_2$ represents hydrogen. Of course, other anhydrides may be used, e.g. benzoic anhydride, to provide compounds wherein $R_1$ represents a radical derived from said other anhydride, e.g. $R_1$ is $OCOC_6H_5$.

An alternative to the above general reaction scheme relies on the Wittig reaction as follows:

(Alkyl)triphenylphosphonium bromide is reacted with 4-bromo-2-thiophene carboxaldehyde in THF, in the presence of potassium tertiary butoxide to yield

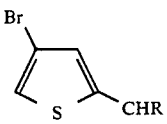

wherein R is an unsaturated alkenyl radical derived from the above alkyl phosphonium bromide. The 2-(alk-1-enyl)-4-bromothiophene of Formula V may be hydrogenated in the presence of Wilkenson's catalyst to yield the saturated derivative. The saturated derivative is consecutively reacted with n-butyl lithium, $SO_2$, NCS and $NH_4OH$/tetra-n-butyl ammoniumfluoride to yield

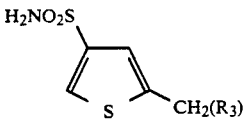

wherein $R_1=R_2=H$ and $R_3$ is alkyl.

Specific compounds within the scope of this invention include:
1-[5-(3-sulfamoyl thienyl)] pentanone oxime
5-(4-hydroxybenzoyl)3-thiophene sulfonamide
5-(3-N,N-dimethylamino-4-hydroxybenzhydrol)-3-thiophene sulfonamide
5-(1-hydroxy-n-pentyl)-3-thiophene sulfonamide
5-(1-hydroxy-n-heptyl)-3-thiophene sulfonamide 5-(4-acetoxymethylbenzhydrol)-3-thiophene sulfonamide
5(4-formylbenzhydrol)-3-thiophene sulfonamide
5-(4-carboxylbenzhydrol)-3-thiophene sulfonamide
5-(benzhydrol)-3-thiophene sulfonamide
5-(4-methoxybenzhydrol)3-thiophene sulfonamide
5-(2-methoxybutyl)-3-thiophene sulfonamide
5-(4-chlorohexyl)-3-thiophene sulfonamide
5-(3-phenylpentyl)-3thiophene sulfonamide
5-(3-methylpentyl)-3-thiophene sulfonamide
5-benzoyl-3-thiophene sulfonamide
5-[benzhydrol]-3-thiophene sulfonamide When administered for the treatment of elevated intraocular pressure of glaucoma, the active compound is most desirably administered topically to the eye, although systemic treatment is also satisfactory.

When given systemically, the drug can be given by any route, although the oral route is preferred. In oral administration the drug can be employed in any of the usual dosage forms such as tablets or capsules, either in a contemporaneous delivery or sustained release form. Any number of the usual excipients or tableting aids can likewise be included.

The active drug of this invention is most suitably administered in the form of ophthalmic pharmaceutical compositions adapted for topical administration to the eye such as a suspension, ointment, or as a solid insert. Formulations of these compounds may contain from 0.01 to 15% and especially 0.5% to 3% of medicament. Higher dosages as, for example, about 10%, or lower dosage can be employed provided the dose is effective in reducing or controlling elevated intraocular pressure. As a unit dosage from 0.001 to 10.0 mg, preferably 0.005 to 2.0 mg, and especially 0.1 to 1.0 mg of the compound is generally applied to the human eye, generally on a daily basis is single or divided doses so long as the condition being treated exists.

The hereinbefore described dosage values are believed accurate for human patients and are based on the known and presently understood pharmacology of the compounds and the activity of other similar entities in the human eye. As with all medications, dosage requirements are variable and must be individualized on the basis of the disease and the response of the patient.

The pharmaceutical preparation which contains the active compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristrate and other conventionally employed acceptable carriers. The pharmaceutical preparation may also contain non-toxic auxiliary substances such as emulsifying, preserving, wetting agents, bodying agents and the like, as for example, polyethylene glycols, antibacterial components such as quaternary ammonium compounds, phenylmercuric salts known to have cold sterilizing properties and which are non-injurious in use, thimerosal, methyl and propyl paraben, benzyl alcohol, buffering ingredients such as sodium chloride, sodium borate, sodium acetate, and other conventional ingredients such as sorbitan monolaurate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The pharmaceutical preparation may also be in the form of a solid insert.

While many patients find liquid medication to be entirely satisfactory, other may prefer a solid medicament that is topically applied to the eye, for example, a solid dosage form that is suitable for insertion into the cul-de-sac. To this end the carbonic anhydrase inhibiting agent can be included with a non-bioerodable insert, i.e., one which after dispensing the drug remains essentially intact, or a bioerodable insert, i.e., one that either is soluble in lacrimal fluids, or otherwise disintegrates.

For example, one may use a solid water soluble polymer as the carrier for the medicament. The polymer used to form the insert may be any water soluble non-toxic polymer, for example, cellulose derivatives such as methylcellulose, sodium carboxymethyl cellulose, or a hydroxy lower alkyl cellulose such as hydroxyethyl cellulose, hydroxypropyl cellulose, hydroxypropylmethyl cellulose and the like; acrylates such as polyacrylic acid salts, ethyl acrylates, polyacrylamides; natural products such as gelatin, alginates, pectins, tragacanth, karaya, chondrus, agar, acacia; the starch derivatives such as starch acetate, hydroxyethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum, and mixtures of said polymers.

The invention is further illustrated by the following examples which are illustrative of a specific mode of practicing the invention and is not intended as limiting the scope of the appended claims.

EXAMPLE 1

2-(n-Hex-1-enyl)-4-bromo thiophene 2.0 grams (10.5 mmols) of (n-pentyl) triphenyl phosphonium bromide was added to 105 ml. of tetrahydrofuran (THF) with stirring. 1.86 gms (15.8 mmol.) of potassium tertiary butoxide was then added to the mixture while stirring at room temperature under an argon atmosphere. After one hour of continued stirring, 2.0 gms (10.5 mmol) of 4-bromo-2-thiophene carboxaldehyde, dissolved in 20 ml of THF, was added to the phosphonium bromide solution. After an additional one hour, the reaction was quenched with water. The organic layer was then separated, washed twice with water and then with brine. After drying over $MgSO_4$ and filtering, the filtrate was concentrated. The concentrate was flushed through a silica plug and eluted with hexane to yield 2.2 gms of a yellow liquid. This liquid included a mixture of cis and trans isomers of the named compound and had the following NMR spectra:

$^1HNMR$ ($CDCl_3$): 7.12 (s), 6.98 (s), 6.88 (s), 6.42 (app. d), 6.03–6.14 (m), 5.52–5.64 (m), 2.32–2.42 (m), 2.12–2.22 (m), 1.28–1.74 (m), 0.90–0.98 (m).

EXAMPLE 2

2-(hexyl)-4-bromo thiophene 2.2 gms (9.0 mmol) of the product of Example 1 were dissolved in 25 ml of ethanol and 0.22 gms of Wilkenson's catalyst were added. (Wilkenson's catalyst is tris(-triphenylphosphine) rhodium (I) chloride.) The mixture was stirred at room temperature under atmospheric hydrogen pressure overnight. The reaction product was concentrated and separated by flash chromatography, using hexane, as the eluant, to yield 2.2 gms of a colorless liquid. The NMR spectra of said liquid was as follows:

$^1$HNMR (CDCl$_3$): 7.01 (s), 6.98 (s), 6.78 (s), 6.71 (s), 6.42 (d, J=15 Hz), 6.09 (d, t, J=8, 15 Hz), 2.77 (t, J=7 Hz), 2.12-2.22 (m), 1.60-1.70 (m), 1.29-1.35 (m), 0.87-0.91 (m).

From said spectra it was determined that 2-(n-hex-1-enyl)-4-bromothiophene was still present in the reaction product. The reaction product was again treated with Wilkenson's Catalyst and hydrogen, overnight. The re-treated reaction mixture was passed through a silica gel plug and eluted with hexane to yield 2.1 gms of a clear, colorless liquid having the following NMR spectra: 7.01 (s, 1H), 6.71 (s, 1H), 2.77 (t=7 Hz, 2H), 1.65 (m, 2H), 1.29-1.35 (m, 6H), 0.89 (t, J=7 Hz, 3H).

EXAMPLE 3

5-n-Heptyl-3-thiophene sulfonamide 1.93 gms (7.8 mmol) of the bromothiophene of Example 2 were added to 78 ml. of THF and the solution was cooled to −100° C., while under an argon atmosphere. 4.9 ml of a 1.6M solution of n-butyl lithium (n-BuLi) in hexane were added to the cooled solution and stirred at −100° C. under an argon atmosphere. After a few minutes, SO$_2$ was bubbled into the solution. When the solution became saturated with SO$_2$, it was allowed to warm to room temperature and 20 ml. of ethyl ether were then added. After about two and one-half hours, the solution was transferred to a roto-evaporator and concentrated. The resulting concentrate was dissolved in 78 ml of methylene dichloride (CH$_2$Cl$_2$) and 1.15 gms (8.6 mmol) of N-chlorosuccinamide (NCS) were added. The resulting mixture was stirred, under argon, at room temperature for two hours. The resulting mixture was filtered and the filtrate was concentrated. The concentrate was dissolved in 50 ml of acetone and 10 ml of concentrate NH$_4$OH (aqueous) were added. After 10 minutes, the mixture was diluted with ethyl acetate and washed with water three times and then with a saturated salt solution, i.e. brine. The organic phase was separated, dried over MgSO$_4$, filtered and the filtrate concentrated. The concentrate was subjected to flash chromatography utilizing a 3 to 1, by volume, mixture of hexane and ethyl acetate eluant to yield 1.24 gms of a light yellow solid having the following NMR spectra:

$^1$H NMR (CDCl$_3$): 7.76 (d, J=1.4 Hz, 1H), 7.07 (d, J=1.4 Hz, 1H), 5.21 (bs, 2H), 2.76 (q, J=7.7 Hz, 2H), 1.65 (p, J=7.7 Hz, 2H), 1.28-1.38 (m, 6H), 0.87 (t, J=6.8 Hz, 3H).

EXAMPLE 3(a)

5-n-Pentyl-3-thiophene sulfonamide

The reactions set forth in Examples 1 through 3 are repeated except that (n-butyl)triphenylphosphine bromide is substituted for (n-pentyl)triphenylphosphine bromide to yield the named compound.

EXAMPLE 3(b)

5-(3-methylpentyl)-3-thiophene sulfonamide

The reactions set forth in Examples 1 through 3 are repeated except that (2-methylbutyl)triphenylphosphine bromide is substituted for (n-pentyl)triphenylphosphine bromide to yield the named compound.

EXAMPLE 3(c)

5-(3-phenylpentyl)-3-thiophene sulfonamide

The reactions set forth in Examples 1 through 3 are repeated except that (2-phenylbutyl)triphenylphosphine bromide is substituted for (n-pentyl)triphenylphosphine bromide to yield the named compound.

EXAMPLE 3(d)

5-(4-chlorohexyl)-3-thiophene sulfonamide

The reactions set forth in Examples 1 through 3 are repeated except that (3-chloropentyl)triphenylphosphine bromide is substituted for (n-pentyl)triphenylphosphine bromide to yield the named compound.

EXAMPLE 3(e)

5-(2-methoxybutyl)-3-thiophene sulfonamide

The reactions set forth in Examples 1 through 3 are repeated except that (3-methoxypropyl)triphenylphosphine bromide is substituted for (n-pentyl)triphenylphosphine bromide to yield the named compound.

EXAMPLE 4

5-[(4-t-butyldimethylsiloxyphenyl)(trimethylsiloxy)methyl]-3-bromothiophene 5.9 gms (0.02 mol) of 4-bromo t-butyldimethylsiloxybenzene were dissolved in 42 ml of dry THF. The solution was cooled to −78° C. while under an argon atmosphere and 13.1 ml (0.02 mol) of a 1.6M solution of n-butyl lithium in hexane were added. After stirring for fifteen minutes under argon the solution was combined over a twenty-five-minute period with a solution of 4.0 gms (0.02 mol) of 4-bromo-2-thiophene carboxaldehyde in 50 ml. of THF at −78° C. The resulting solution was stirred for one hour and fifteen minutes at −78° C. 1.95 ml of trimethylsilylchloride (TMSCl) were added and the solution was allowed to warm to room temperature overnight with stirring. An additional 10 ml of TMSCl were added and the solution was stirred for six hours. The reaction was quenched with water; the organic phase was separated from the brine, dried over MgSO$_4$, filtered, concentrated and separated by flash chromatography, utilizing hexane as the eluant. 2.5 gms of a clear colorless liquid were recovered having an NMR spectra of:

$^1$H NMR (acetone-d$^6$): 7.21 (d, J=8.5 Hz, 2H), 7.11 (d, J=1.5 Hz, 1H), 6.80 (d, J=8.5 Hz, 2H), 6.65 (d, J=1.5 Hz, 1H), 5.84 (s, 1H), 0.99 (s, 3H), 0.21 (s, 6H), 0.10 (s, 9H).

EXAMPLE 5

5-(4-hydroxybenzhydrol)3-thiophene sulfonamide 2.34 gms (5.0 mmol) of the bromothiophene, prepared in Example 4, were dissolved in 50 ml of dry THF. The resulting solution is cooled to −78° C. while under an argon atmosphere. 3.1 ml of a 1.6M solution of n-BuLi, in hexane, is added and stirring was continued for a few minutes. SO$_2$ was bubbled into the solution until the solution was saturated with SO$_2$. 20 ml of ethyl ether were added and the solution was allowed to warm to room temperature. After about two hours at room temperature, the solution was concentrated, the residue dissolved in 50 ml of methylene dichloride and 0.73 gms (5.5 mmol) of NCS were added. After about one-half hour, the resulting mixture was filtered, the filtrate concentrated and the concentrate was dissolved in a solution of 5 ml concentrated NH4OH (aqueous) and 25 ml of acetone. After one-half hour, the resulting solution is diluted with ethyl acetate, washed with water, three times, and then with brine. The resulting organic phase is separated, dried over MgSO4, filtered and the filtrate concentrated. The concentrate was subjected to flash chromatography utilizing a 3:1 mixture of hexane and ethyl acetate, as the eluant, to yield 1.41 gms of a light yellow oil having the following NMR spectra:

$^1$H NMR (acetone-d$^6$): 7.88 (s, 1H), 7.33 (d, J=9 Hz, 2H), 7.10 (s, 1H), 6.88 (d, J=9 Hz, 2H), 6.55 (bs, 2H), 6.07 (s, 1H), 0.97 (s, 9H), 0.20 (s, 6H), 0.07 (s, 9H).

0.52 gms (1.1 mmol.) of the product light yellow oil was dissolved in 11 ml of THF and 2.3 ml of a 1.0M solution of tetra-n-butyl ammonium fluoride (TBAF) in THF is added. After one-half hour, the reaction was quenched with water and extracted with ethyl acetate. The organic layer was separated, washed three times with water and then with brine. The organic phase was separated, dried over MgSO4, filtered and the filtrate concentrated. The concentrate was subjected to flash chromatography, utilizing the above hexane/ethyl acetate mixture to yield 0.26 gms of a white foam having the following NMR spectra:

$^1$H NMR (acetone-d$^6$): 8.43 (bs, 1H), 7.88 (s, 1H), 7.28 (d, J=9 Hz, 2H), 7.05 (s, 1H), 6.82 (d, J=9 Hz, 2H), 6.57 (bs, 2H), 5.95 (s, 1H), 5.32 (bs, 1H).

EXAMPLE 5(a)

5-(4-methoxybenzhydrol)-3-thiophene sulfonamide

The reactions set forth in Examples 4 and 5 are repeated except that 4-methoxybromobenzene is substituted for 4-bromo t-butyldimethyl-siloxy-benzene to yield the named compound which has the following NMR spectra:

$^1$H NMR (acetone-d$^6$): 7.88 (d, J=1.5 Hz, 1H), 7.38 (d, J=8.6 Hz, 2H), 7.07 (m, 1H), 6.92 (d, J=8.6 Hz, 2H), 6.54 (bs, 2H), 5.99 (d, J=4.3 Hz, 1H), 5.34 (d, J=4.3 Hz, 1H), 3.78 (s, 3H).

EXAMPLE 5(b)

5-(benzhydrol)-3-thiophene sulfonamide

The reactions set forth in Examples 4 and 5 are repeated except that bromobenzene is substituted for 4-bromo t-butyldimethylsiloxybenzene to yield the named compound. This compound may be subsequently reacted with acetic anhydride in the presence of pyridine, as described above, to yield the acylated derivative, i.e. 5-[(phenyl)(acetoxy)methyl]-3-thiophene sulfonamide, having the following NMR spectra:

$^1$H NMR (acetone-d$^6$): 7.90 (s, 1H), 7.30–7.50 (m, 5H), 7.10 (s, 1H), 6.55 (bs, 2H), 6.05 (d, J=4.3 Hz, 1H), 5.46 (d, J=4.3 Hz, 1H).

EXAMPLE 5(c)

5-(1-hydroxy-n-heptyl)-3-thiophene sulfonamide

The reactions set forth in Examples 4 and 5 are repeated except that 1-bromohexane is substituted for 4-bromo t-butyldiimethylsiloxybenzene to yield the named compound, having the following NMR spectra:

$^1$H NMR (CDCl$_3$): 7.88 (s, 1H), 7.24 (s, 1H), 5.06 (bs, 2H), 4.88–4.89 (m, 1H), 2.43–2.45 (m, 1H), 1.79–1.81 (m, 2H), 1.25–1.31 (m, 8H), 0.86–0.88 (m, 3H).

EXAMPLE 5(d)

5-(1-hydroxy-n-pentyl)-3-thiophene sulfonamide

The reactions set forth in Examples 4 and 5 are repeated except that 1-bromobutane is substituted for 4-bromo t-butyldimethylsiloxybenzene to yield the named compound, having the following NMR spectra:

$^1$H NMR (CDCl$_3$): 7.82 (s, 1H), 7.20 (s, 1H), 5.35 (bs, 2H), 4.80 (t, J=4.5 Hz, 1H), 1.70–2.88 (m, 2H), 1.24–1.48 (m, 4H), 0.88 (t, J=4.5 Hz, 3H).

EXAMPLE 5(e)

5-(3-hydroxybenzhydrol)-3-thiophene sulfonamide

The reactions set forth in Examples 4 and 5 are repeated except that 3-bromo t-butyldimethylsiloxy is substituted for 4-bromo t-butyldi-methylsiloxybenzene to yield the named compound, having the following NMR spectra:

$^1$H NMR (acetone-d$^6$): 8.40 (bs, 1H), 7.89 (d, J=1.5 Hz, 1H), 7.18 (t, J=7.7 Hz, 1H), 7.11 (d, J=1.5 Hz, 1H), 6.92–6.97 (m, 2H), 6.75–6.78 (m, 1H), 6.56 (bs, 2H), 5.97 (s, 1H), 5.40 (bs, 1H).

EXAMPLE 6

5-(4-hydroxybenzoyl)-3-thiophene sulfonamide 0.10 gms (0.35 mmol) of 5-(4-hydroxybenzhydrol) 3-thiphene sulfonamide, as prepared in Example 5, were dissolved in 5 ml of acetone and to this solution 0.13 ml (0.35 mmol) of a 2.67M solution of Jones' Reagent were added. (Jones' Reagent is aqueous chromic acid.) The resulting mixture was stirred for about forty minutes at room temperature and then quenched with isopropyl alcohol. The resulting solution was diluted with ethyl acetate, washed three times with water and then with brine. The organic layer was separated, dried over MgSO4, filtered and the filtrate concentrated. The concentrate was subjected to flash chromatography, utilizing a 1:1 mixture of hexane and ethyl acetate, as the eluant, to yield 78 mg of a clear colorless oil having the following NMR spectra:

$^1$H NMR (acetone-d$^6$): 9.45 (bs, 1H), 8.43 (d, J=1.3 Hz, 1H), 7.95 (d, J=1.3 Hz, 1H), 7.89 (d, J=9 Hz, 2H), 7.04 (d, J=9 Hz, 2H), 6.81 (bs, 2H).

EXAMPLES 6(a)–(j)

The compounds of Examples 5(a)–(j) are converted into the corresponding alpha carbonyl derivatives by the method of Example 6. The compounds were identified by the NMR spectra given below.

EXAMPLE 6(a)

5-(4-methoxybenzoyl)-3-thiophene sulfonamide $^1$H NMR (acetone-d$^6$): 8.43 (s, 1H), 7.92–7.95 (m, 3H), 7.12 (d, J=9.0 Hz, 2H), 6.77 (bs, 2H), 3.93 (s, 3H).

EXAMPLE 6(b)

5-benzoyl-3-thiophene sulfonamide $^1$H NMR (acetone-d$^6$): 8.48 (s, 1H), 7.90–7.95 (m, 3H), 7.60–7.75 (m, 3H), 6.80 (2H).

EXAMPLE 6(c)

5-(1-heptanoyl)-3-thiophene sulfonamide $^1$H NMR (CDCl$_3$): 8.21 (s, 1H), 7.94 (s, 1H), 5.01 (bs, 2H), 2.89 (t, J=7.3 Hz, 2H), 1.73 (p, 7.2 Hz, 2H), 1.30–1.34 (m, 6H), 0.88 (t, J=8.3 Hz, 3H).

EXAMPLE 6(d)

5-(1-pentanoyl)-3-thiophene sulfonamide $^1$H NMR (CDCl$_3$): 8.22 (s, 1H), 7.96 (s, 1H), 5.10 (bs, 2H), 2.90 (t, J=7.5 Hz, 2H), 1.73 (p, J=7.5 Hz, 2H), 1.40 (sex., J=7.5 Hz, 2H), 0.95 (t, J=7.5 Hz, 3H).

EXAMPLE 6(e)

5-(3-hydroxybenzoyl)-3-thiophene sulfonamide $^1$H NMR (acetone-d$^6$): 8.46 (d, J=1.3 Hz, 1H), 7.93 (d, J=1.4 Hz, 1H), 7.32–7.46 (m, 3H), 7.15–7.19 (m, 1H), 6.86 (bs, 2H).

Examples 6(f) to (j) were prepared by a process analogous to the preparation of Examples 6(a) to (e) with the appropriate bromo reactant substituted for the 4-bromotrimethylsiloxybenzene.

EXAMPLE 6(f)

5-(4-butylbenzoyl)-3-thiophene sulfonamide $^1$H NMR (acetone-d$^6$): 8.45 (d, J=1.4 Hz, 1H), 7.93 (d, J=1.4 Hz, 1H), 7.85 (d, J=8.2 Hz, 2H), 7.45 (d, J=8.2 Hz, 2H), 6.78 (bs, 2H), 2.74 (t, J=7.5 Hz, 2H), 1.60–1.68 (m, 2H), 1.38 (sex., J=7.8 Hz, 2H), 0.93 (t, J=7.3 Hz, 3H).

EXAMPLE 6(g)

5-(3-trifluoromethylbenzoyl)-3-thiophene sulfonamide $^1$H NMR (acetone-d$^6$): 8.52 (d, J=1.4 Hz, 1H), 8.22 (d, J=7.9 Hz, 1H), 8.17 (s, 1H), 8.06 (d, J=8.3 Hz, 1H), 7.95 (d, J=1.4 Hz, 1H), 7.88 (t, J=7.8 Hz, 1H), 6.78 (bs, 2H).

EXAMPLE 6(h)

5-(2-fluorobenzoyl)-3-thiophene sulfonamide $^1$H NMR (acetone-d$^6$): 8.50 (d, J=1.2 Hz, 1H), 7.79 (t, J=1.5 Hz, 1H), 7.68–7.73 (m, 2H), 7.34–7.44 (m, 2H), 6.80 (bs, 2H).

EXAMPLE 6(i)

5-(3-fluorobenzoyl)-3-thiophene sulfonamide $^1$H NMR (acetone-d$^6$): 8.49 (s, 1H), 7.95 (s, 1H), 7.60–7.77 (m, 3H), 7.47–7.53 (m, 1H), 6.79 (bs, 2H).

EXAMPLE 6(j)

5-(3.5-difluorobenzoyl)-3-thiophene sulfonamide $^1$H NMR (acetone-d$^6$): 8.51 (s, 1H), 7.99 (s, 1H), 7.49–7.56 (m, 2H), 7.37–7.44 (m, 2H), 6.79 (bs, 2H).

EXAMPLE 7

5-(4-hydroxy-3-(N,N-dimethylaminomethyl)benzoyl)-3-thiophene sulfonamide 5-(4-hydroxy-3,5-(bis-N,N-dimethylaminomethyl)benzoyl)-3-thiophene sulfonamide 0.25 g (0.88 mmol) of 5-(4-hydroxybenzoyl)-3-thiophene sulfonamide, 0.21 mL (2.6 mmol) of aqueous formaldehyde (37%) and 0.89 mL (7.9 mmol) of aqueous dimethylamine (40%) were added to 3 mL of ethanol. The solution was heated at reflux for 15 ½ h and then cool to room temperature. Solvent was removed under vacuum and the crude product subjected to flash chromatography. Utilizing 5:1 chloroform/methanol as the eludent 49 mg of 5-(4-hydroxy-3-(N,N-dimethylaminomethyl)benzoyl)-3-thiophene sulfonamide was recovered as a yellow color solid.

$^1$H NMR (acetone-d$^6$): 8.39 (d, J=1.4 Hz, 1H), 7.92 (d, J=1.4 Hz, 1H), 7.81 (dd, J=8.5, 2.3 Hz, 1H), 7.67 (d, J=2.3 Hz, 1H), 6.85 (d, J=8.5 Hz, 1H), 3.82 (s, 2H), 2.38 (s, 6H).

The eluant was switched over to 2:1 methanol/chloroform (with 5% triethylamine) and 0.18 g of 5-(4-hydroxy-3,5-(bis-N,N-dimethylamino-methyl)benzoyl)-3-thiophene sulfonamide was recovered as a yellow color solid.

$^1$H NMR (acetone-d$^6$): 8.39 (d, J=1.4 Hz, 1H), 7.93 (d, J=1.4 Hz, 1H), 7.75 (s, 2H), 3.66 (s, 4H), 2.32(s, 12H).

EXAMPLE 8

4-bromo-2-[tetrahydropyronyl) (4-t-butyldimethylsiloxymethylphenyl)methyl] thiophene 6.5 g (22 mmol) of 4-bromobenzyl alcohol, t-butyldimethylsilyl ether was added to 40 mL of THF. The solution was cool to −78° C. 15.3 mL (22 mmol) of a 1.42M n-BuLi solution was added. The solution was transferred via cannula to 4.2 g (22 mmol) of 4-bromo-2-thiophene carboxaldehyde in 70 mL THF at −78° C. Reaction was stirred at −78° C. for 30 min before quenching with 5 mL of saturated NH$_4$Cl. The reaction was diluted with ethyl acetate and washed with water (3×) followed with brine. Solution was dried over MgSO$_4$ and the solvent removed under vacuum. The product, 10 mL (o.11 mol) of DHP and a catalytic amount of TsOH were added to 88 mL of dichloromethane. The reaction was stirred at rt for 18 ½ h. The reaction was washed with water (3×) followed with brine. The solution was dried over MgSO$_4$ and the solvent removed under vacuum. Flash chromatography utilizing 20:1 hexane/ethyl ether as the eluant recovered 9.3 g of the product as a light yellow color oil.

$^1$H NMR (CDCl$_3$): mixture of diastereomers; 7.27–7.40 (m), 7.12–7.18 (m), 6.90 (s), 6.58 (s), 5.95 (s), 5.90 (s), 4.84–4.88 (m), 4.75 (s), 4.72 (s), 4.62–4.66 (m), 3.96–4.05 (m), 3.74–3.82 (m), 3.48–3.62 (m), 1.48–2.02 (m), 0.94 (s), 0.93 (s), 0.12 (s), 0.10 (s).

EXAMPLE 9

5-[(tetrahydropyranyl)(4-t-butyldimethylsiloxymethylphenyl)methyl]-3-thiophene sulfonamide 8.8 g (18 mmol) of the product obtained in Example #8 was added to 180 mL of THF. The solution was cool to −100° C. 12.7 mL (18 mmol) of a 1.42M n-BuLi solution was added dropwise. After a few minutes SO$_2$ was passed through the reaction flask until the solution became saturated. 30 mL of ethyl ether was added and the liquid nitrogen/ethyl ether bath removed. After 2 h the solvent was removed under vacuum. The crude product and 2.6 g (19.8 mmol) NCS were added to 180 mL of dichloromethane. After stirring at rt for 1½ h the mixture was filtered and the filtrate concentrated. The crude product was added to 30 mL of concentrated ammonium hydroxide in 180 mL of acetone. Upon stirring for 3½ h the solution was dilutd with ethyl acetate and washed with water (3×) followed with brine. The solution was dried over MgSO$_4$ and the solvent removed under vacuum. Flash chromatography utilizing 2:1 hexane/ethyl acetate recovered 2.9 g of the product as a yellow color oil.

$^1$H NMR (CDCl$_3$): mixture of diastereomers; 7.96 (s), 7.94 (s), 7.49–7.34 (m), 7.01 (s), 6.07 (s), 6.01 (s), 4.83–4.86 (m), 4.78 (s), 4.60–4.64 (m), 3.90–3.99 (m), 3.68–3.77 (m), 3.43–3.58 (m), 1.43–1.98 (m), 0.96 (s), 0.15 (s), 0.13 (s).

EXAMPLE 10

5-(4-hydroxymethylbenzhydrol)-3-thiophene sulfonamide 0.36 g (0.72 mmol) of the product from Example #9 and a catalytic amount of TsOH were added to 10 mL of methanol. After 2 h of stirring at rt the solution was diluted with ethyl acetate and washed with water (3×) followed with brine. The solution was dried over MgSO4 and the solvent removed under vacuum. Flash chromatography utilizing 2:1 ethyl acetate/hexane as the eluant recovered 87 mg of 5-(4-hydroxymethylbenzhydrol)-3-thiophene sulfonamide as a clear colorless oil.

$^1$H NMR (acetone-d$^6$): 7.88 (d, J=1.4 Hz, 1H), 7.44 (d, J=7.5 Hz, 2H), 7.35 (d, J=7.5 Hz, 2H), 7.08 (d, J=1.4 Hz, 1H), 6.54 (bs, 2H), 6.04 (d, J=4.3 Hz, 1H), 5.42 (d, J=4.3 Hz, 1H), 4.62 (d, J=5.7 Hz, 2H), 4.19 (t, J=5.8 Hz, 1H).

EXAMPLE 11

5-(4-carboxybenzoyl)-3-thiophene sulfonamide 0.53 g (1.8 mmol) of 5-(4-hydroxymethylbenzhydrol)-3-thiophene sulfonamide was added to 8.8 mL of acetone. The solution was cool to 0° C. and 1.35 mL (3.7 mmol) of Jone's reagent was added. After 15 min the solvent was removed under vacuum and the mixture filtered. The solid was washed with water. Flash chromatography utiling 20% methanol/chloroform as the eluant recovered 0.48 g of 5-(4-carboxybenzoyl)-3-thiophene sulfonamide as a white solid.

$^1$H NMR (acetone-d$^6$): 8.51 (d, J=1.4 Hz, 1H), 8.23 (d, J=8.3 Hz, 2H), 8.01 (d, J=8.3 Hz, 2H), 7.94 (d, J=1.4 Hz, 1H),6.79 (bs, 2H).

EXAMPLE 11(a)

5-(3-carboxylbenzoyl)-3-thiophene sulfonamide $^1$H NMR (acetone-d$^6$): 8.51 (d, J=1.4 Hz, 1H), 8.50 (s, 1H), 8.34 (d, t, J=7.8, 1.3 Hz, 1H), 8.16 (d, t, J=7.8, 1.3 Hz, 1H), 7.96 (d, J=1.3 Hz, 1H), 7.77 (t, J=7.8 Hz, 1H), 6.81 (bs, 2H).

EXAMPLE 12

5-[(tetrahydropyranyl)(4-hydroxymethylphenyl)methyl]-3-thiphene sulfonamide 0.45 g (0.91 mmol) of the product from Example #9 was added to 10 mL of THF. 1.0 mL (1.0 mmol) of a 1M tetra-n-butylammonium fluoride solution was added. After stirring at rt for 1 h the solution was diluted with water and extracted with ethyl acetate. The organic phase was washed with water (3×) followed with brine. The solution was dried over MgSO4 and the solvent removed under vacuum. Flash chromatography utilizing 1:1 hexane/ethyl acetate as the eluent recovered 0.33 g of the product as a clear colorless oil.

$^1$H NMR (acetone-d$^6$): mixture of diastereomers; 7.97 (s), 7.95 (s), 7.32–7.48 (s), 6.97 (s), 6.60 (bs), 6.55 (bs), 6.05 (s), 5.98 (s), 4.82–4.85 (m), 4.58–4.68 (m), 4.17–4.28 (m), 3.90–3.97 (m), 3.68–3.75 (m), 3.40–3.56 (m), 1.44–1.98 (m).

EXAMPLE 13

5-(4-acetoxymethylbenzhydrol)-3-thiophene sulfonamide 0.74 g (1.9 mmol) of the product from Example #12, 0.23 mL (2.9 mmol) of pyridine and 0.23 mL (2.9 mmol) of acetic anhydride were added to 19 mL of dichloromethane. After stirring at rt for 15 h the solution was diluted with ethyl acetate and washed with water (3×) followed with brine. The solution was dried over MgSO4 and the solvent removed under vacuum. The 0.60 g of the crude product and a catalytic amount of TsOH were added to 14 mL of methanol. After stirring at rt for 3½ h the solution was diluted with water and extracted with ethyl acetate. The organic phase was washed with water (2×) followed with brine. The solution was dried over MgSO4 and the solvent removed under vacuum. Flash chromatography utilizing 1:1 hexane/ethyl acetate as the eluant recovered 0.37 g of 5-(4-acetoxymethyl-benzhydrol)-3-thiophene sulfonamide as a clear colorless oil.

$^1$H NMR (acetone-d$^6$): 7.90 (s, 1H), 7.48 (d, J=7.5 Hz, 2H), 7.37 (d, J=7.5 Hz, 2H), 7.12 (s, 1H), 6.55 (bs, 2H), 6.08 (s, 1H), 5.50 (bs, 1H), 5.10 (s, 2H), 2.08 (s, 3H).

EXAMPLE 14

5-(4-acetoxymethylbenzoyl)-3-thiophene sulfonamide 0.20 g (0.6 mmol) of 5-(4-acetoxymethylbenzhydrol)-3-thiophene sulfonamide was added to 6 mL of acetone. 0.22 mL (0.6 mmol) of a 2.67M TBAF solution was added. After stirring at rt for 15 min the reaction was quenched with isopropyl alcohol. The mixture was diluted with water and extracted with ethyl acetate. The organic phase was washed with water (3×) followed with brine. The solution was dried over MgSO4 and the solvent removed under vacuum. Recrystallization from ethyl acetate/hexane afforded 0.17 g of 5-(4-acetoxymethylbenzoyl)-3-thiophene sulfonamide as white crystals.

$^1$H NMR (acetone-d$^6$): 8.47 (d, J=1.4 Hz, 1H), 7.93 (s, 1H), 7.92 (d, J=8.3 Hz, 2H), 7.62 (d, J=8.3 Hz, 2H, 6.80 (bs, 2H), 5.22 (s, 2H), 2.10 (s, 3H).

EXAMPLE 15

5-(4-hydroxymethylbenzoyl)-3-thiophene sulfonamide 14 mg (41.3 mmol) of 5-(4-acetoxymethylbenzoyl)-3-thiophene sulfonamide and 9 mg (61.8 mmol) of K$_2$CO$_3$ were added to 3 mL of methanol. After stirring at rt for 11 h the solution was diluted with ethyl acetate and washed with 1N HCl followed with water (2×) and brine. The solvent was removed under vacuum to afford 12.5 mg of 5-(4-hydroxymethylbenzoyl)-3-thiophene sulfonamide as a white solid.

$^1$H NMR(acetone-d$^6$): 8.46 (d, J=1.4 Hz, 1H), 7.93 (d, J=1.4 Hz, 1H), 7.89 (d, J=8.3 Hz, 2H), 7.59 (d, J=7.9 Hz, 2H), 6.79 (bs, 2H), 4.77 (d, J=5.4 Hz, 2H), 4.51 (t, J=5.7 Hz, 1H).

EXAMPLE 16

5-(4-formylbenzoyl)-3-thiophene sulfonamide 30 mg (0.1 mmol) of 5-(4-hydroxymethylbenzoyl)-3-thiophene sulfonamide and 300 mg of MnO2 were added to 5 mL of THF. After stirring at rt for 30 min the mixture was filtered through a bed of celite and eluted with ethyl acetate. The filtrate was concentrated and the crude product subjected to flash chromatography utilizing 1:1 ethyl acetate/hexane as the eluent to recover 16 mg of 5-(4-formylbenzoyl)-3-thiophene sulfonamide as a yellow solid.

$^1$H NMR(acetone-d$^6$): 10.21 (s, 1H), 8.52 (d, J=1.3 Hz, 1H), 8.12 (q, J=9.7 Hz, 4H), 7.94 (d, J=1.3 Hz, 1H), 6.79 (bs, 2H).

EXAMPLE 16(a)

5-(3-formylbenzoyl)-3-thiophene sulfonamide $^1$H NMR(acetone-d6): 10.18 (s, 1H), 8.52 (d, J=1.3 Hz, 1H), 8.14 (s, 1H), 8.23 (d, t, J=1.4, 8.0 Hz, 2H), 7.97 (d, J=1.4 Hz, 1H), 7.85 (t, J=8.0 Hz, 1H), 6.80 (bs, 2H).

EXAMPLE 17

5-(4-formylbenzhydrol)-3-thiophene sulfonamide 0.12 g (0.32 mmol) of the product from Example #12, 4A molecular sieves and 56 mg (0.48 mmol) of NMO were added to 6 mL of dichloromethane. After stirring at rt for 15 min 5.6 mg (0.016 mmol) of TPAP was added. After 4 h at rt the mixture was filtered through a plug of celite and eluted with ethyl acetate. The filtrate was concentrated and the crude product subjected to flash chromatography utilizing 1:1 ethyl acetate/hexane as eluant to recover 42 mg of the desired product and 41 mg of starting material.

63 mg (0.17 mmol) of the product and a catalytic amount of TsOH were added to 5 mL of methanol. After 4 h at rt the solution was diluted with ethyl acetate and washed with saturated NaHCO$_3$ followed with water (3×) and brine. The solution was dried over MgSO$_4$ and the solvent removed under vacuum to afford 47 mg of 5-(4-formylbenzhydrol)-3-thiophene sulfonamide as a clear colorless oil.

$^1$H NMR(acetone-d$^6$): 10.04 (s, 1H), 7.94 (d, J=8.3 Hz, 2H), 7.93 (s, 1H), 7.73 (d, J=8.3 Hz, 2H), 7.18 (s, 1H), 6.58 (bs, 2H), 6.20 (d, J=4 Hz, 1H), 5.77 (d, J=4 Hz, 1H).

EXAMPLE 18

5-[(methoxy)(3-trifluoromethylphenyl)methyl]-3-thiophene sulfonamide 0.20 g (0.6 mmol) of 5-(3-trifluoromethylbenzhydrol)-3-thiophene sulfonamide and 0.11 g (0.6 mmol) of TsOH were added to 10 mL of methanol. The solution was heated at reflux for 12 h. The solvent was removed under vacuum and the crude product subjected to flash chromatography utilizing 2:1 hexane/ethyl acetate as the eluant to recover 0.16 g of 5-[(methoxy)(3-trifluoromethylphenyl)methyl]-3-thiophene sulfonamide as a white solid.

$^1$H NMR (acetone-d$^6$): 7.99 (d, J=1.5 Hz, 1H), 7.66-7.80 (m, 4H), 7.23-7.24 (m, 1H), 6.59 (bs, 2H), 5.76 (s, 1H), 3.41 (s, 3H).

EXAMPLE 18(a)

5-[(methoxy)(4-hydroxymethylphenyl)]methyl-3-thiophene sulfonamide $^1$H NMR (acetone-d$^6$): 7.94 (d, J=1.1 Hz, 1H), 7.39 (s, 4H), 7.08 (d, J=1.1 Hz, 1H), 6.56 (bs, 2H), 5.56 (s, 1H), 4.64 (d, J=5.9 Hz, 2H), 4.24 (t, J=5.9 Hz, 1H), 3.35 (s, 3H).

EXAMPLE 19

5-(1-pentanoyl)-3-thiophene sulfonamide, oxime 0.10 gms (0.4 mmol) of 5-(1-pentanoyl)-3-thiophene sulfonamide and 0.28 gms (4 mmol) of NH$_2$OH.HCl were dissolved in 5 ml of pyridine. The reaction vessel was sealed and heated at 60° C. overnight. The reaction solution was cooled to room temperature, diluted with ethyl acetate, washed three times with water and finally with brine. The organic phase was separated, dried over MgSO$_4$, filtered and concentrated. Thin liquid chromatography showed that the starting compounds were present. The concentrate was redissolved in 5 ml of pyridine, 0.25 gms of NH$_2$OH.HCl were added and the reaction vessel was sealed and heated at 60° C. overnight. The resulting reaction solution was cooled to room temperature, extracted with ethyl acetate, washed with water and brine as described above. After drying with MgSO$_4$ and filtering, the organic phase was concentrated and subjected to flash chromatography, utilizing a 2 to 1 mixture of hexane and ethyl acetate, as the eluant, to yield 78 mgs. of a white solid having the following NMR spectra:

$^1$H NMR (acetone-d$^6$): mixture of Isomers: 11.11 (bs), 10.50 (bs), 8.16 (s), 7.92 (s), 7.78 (s), 7.55 (s), 6.64 (bs), 2.68-2.80 (m), 1.35-1.67 (m), 0.89-0.95 (m).

EXAMPLES 19(a)-(b)

The compounds of Examples 6(a) and (b) are converted into the corresponding oxime derivatives by the method of Example 19.

EXAMPLE 19(a)

5-(4-methoxybenzoyl)-3-thiophene sulfonamide, oxime $^1$H NMR (acetone-d$^6$): 11.55 (s), 10.58 (s), 8.22 (d, J=1.4 Hz), 7.96 (d, J=1.4 Hz), 7.40-7.47 (m), 7.00-7.07 (m), 6.61-6.64 (m), 3.87 (s), 3.86 (s).

EXAMPLE 19(b)

5-benzoyl-3-thiophene sulfonamide, oxime $^1$H NMR (acetone-d$^6$): mixture of Isomers: 11.69 (bs), 10.65 (bs), 8.24 (d, J=1.4 Hz), 7.98 (d, J=1.4 Hz), 7.37-7.59 (m), 7.02 (d, J=1.4 Hz), 6.58-6.64 (m).

EXAMPLE 20

5-(4-ethoxycarbonylbenzoyl)-3-thiophene sulfonamide 0.1 g (0.32 mmol) of 5-(4-carboxylbenzoyl)-3-thiophene sulfonamide was added to 0.19 g (1.13 mmol) of N,N'-diisopropyl-O-ethyl isourea 1.6 mL of THF. Solution was heated at 50° C. for 2 h. An additional 0.19 g of the isourea was added and the reaction stirred at 50° C. for 48 h. The mixture was filtered through a plug of celite and the filtrate collected and concentrated. Flash chromatography (35% ethyl acetate/hexane) recovered 80 mg of 5-(4-ethoxycarbonylbenzoyl)-3-thiophene sulfonamide as a white color solid.

$^1$H NMR (acetone-d$^6$): 8.50 (d, J=1.4 Hz, 1H), 8.20 (d, J=8 Hz, 2H), 8.10 (d, J=8 Hz, 2H), 7.92 (d, J=1.4 Hz, 1H), 6.80 (bs, 2H), 4.40 (q, J=7 Hz, 2H), 1.39 (t, J=7 Hz, 3H).

EXAMPLE 20(a)

5-(3-butoxycarbonylbenzoyl)-3-thiophene sulfonamide 8.50 (d, J=1.4 Hz, 1H), 8.43 (m, 1H), 8.25 (m, 1H), 8.12 (m 1H), 7.94 (d, J=1.4 Hz, 1H), 7.74 (m, 1H), 6.80 (bs, 2H), 1.60 (s, 9H).

EXAMPLE 20(b)

5-(4-(2-N,N-dimethylamino-1-ethoxy)carbonylbenzoyl)-3-thiophene sulfonamide $^1$H NMR (CD$^3$OD):

8.47 (d, J=1.4 Hz, 1H), 8.29 (d, J=8.5 Hz, 2H), 8.00 (d, J=8.5 Hz, 2H), 7.89 (d, J=1.4 Hz, 1H), 4.73 (t, J=5 Hz, 2H), 3.65 (t, J=5 Hz, 2H), 3.03 (s, 6H).

EXAMPLE 20(c)

5-(4-t-butoxycarbonylbenzoyl)-3-thiophene sulfonamide $^1$H NMR (acetone-d$^6$):
8.50 (d, J=1.4 Hz, 1H), 8.16 (d, J=8.5 Hz, 2H), 8.00 (d, J=8.5 Hz, 2H), 7.93 (d, J=1.4 Hz, 1H), 6.79 (bs, 2H), 1.61 (s, 9H).

EXAMPLE 21

5-(4-acetoxybenzoyl)-3-thiophene sulfonamide 58 mg (0.20 mmol) of 5-(4-hydroxybenzoyl)-3-thiophene sulfonamide, 81 mL (1.0 mmol) of pyridine and 94 mL (1.0 mmol) of acetic anhydride were added to 4 mL of THF. The reaction was stirred at rt for 1 ¼ h and then diluted with ethyl acetate. The organic phase was washed with water (2×) followed with brine. The solution was dried over MgSO$_4$ and the solvent removed under vacuum. Flash chromatography utilizing 1:1 hexane/ethyl acetate as the eluant recovered 51 mg of 5-(4-acetoxybenzoyl)-3-thiophene sulfonamide as tan color crystals.

$^1$H NMR (acetone-d$^6$):
8.47 (d, J=1.3 Hz, 1H), 7.98 (d, J=8.6 Hz, 2H), 7.96 (d, J=1.3 Hz, 1H), 7.37 (d, J=8.6 Hz, 2H), 6.78 (bs, 2H), 2.32 (s, 3H).

EXAMPLE 21(a)

5-(3-acetoxybenzoyl)-3-thiophene sulfonamide $^1$H NMR (acetone-d$^6$):
8.22 (d, J=1.3 Hz, 1H), 7.69 (d, J=1.3 Hz, 1H), 7.53 (d,d, J=7.8, 1.3 Hz, 1H), 7.37 (t, J=7.8 Hz, 1H), 7.39 (s, 1H), 7.18-7.22 (m, 1H), 6.50 (bs, 2H), 2.04 (s, 3H).

EXAMPLE 22

5-(4-propionoxybenzoyl)-3-thiophene sulfonamide 0.10 g (0.35 mmol) of 5-(4-hydroxybenzoyl)-3-thiophene sulfonamide, 85 mL (1.05 mmol) of pyridine, 26 mL (0.35 mmol) of propionic acid and 70 mg (0.37 mmol) of EDCI were added to 3.5 mL of THF. The reaction was stirred at rt for 46 h. The solution was diluted with ethyl acetate and washed with water (3×) followed with brine. The solution was dried over MgSO4 and the solvent removed under vacuum. Flash chromatography utilizing 1:1 ethyl acetate/hexane recovered 77 mg of 5-(4-propionoxybenzoyl)-3-thiophene sulfonamide as a clear colorless oil.

$^1$H NMR (acetone-d$^6$):
8.47 (s, 1H), 7.99 (d, J=8.7 Hz, 2H), 7.95 (s, 1H), 6.79 (bs, 2H), 2.67 (q, J=7.4 Hz, 2H), 1.21 (t, J=7.4 Hz, 3H).

EXAMPLE 22(a)

5-(3-benzoxybenzoyl)-3-thiophene sulfonamide $^1$H NMR (acetone-d$^6$): 8.50 (d, J=1.4 Hz, 1H), 8.21 (d, J=7.2 Hz, 2H), 8.00 (d, J=1.4 Hz, 1H), 7.59-7.88 (m, 7H), 6.78 (bs, 2H).

The compounds of the invention were assayed for biological activity as follows:

Carbonic anhydrase activity was assayed according to the micromethod of Maren (*J. Pharmacol. Exptl. Therap.*, 130, 26-29, 1960). All solutions and reagents were maintained at 0°-4° C. The final assay mixture contained 16 mM phenol red, added enzyme and 62.5 mM sodium carbonate/bicarbonate. Its volume was kept constant at 0.8 mL. The time required for the added enzyme to lower the pH of $CO_2$-saturated carbonate/bicarbonate buffer from pH 9.9 to 6.8 was measured using the color change of phenol red as endpoint. $T_1$ is the time recorded for the reaction containing no enzyme. $T_2$ is the time recorded for the reaction containing pure CA11 enzyme from human erythrocyte, or an unknown amount in a sample. Enzyme activities (unit) were calculated using the formula:

$$\text{Unit/ug} = (T_1 - T_2)/(T_2 * \text{ug protein used in assay})$$

IC50 of a carbonic anhydrase inhibitor is the concentration that lowers the enzyme activity to half.

The results of this assay are reported in Table 1, below.

| Structures | IC50nM |
|---|---|
| 5-(4-acetoxybenzoyl)-3-thiophene sulfonamide | 12 nM |
| 5-(4-hydroxy-3-(N,N-dimethylaminomethyl) benzoyl)-3-thiophene sulfonamide | 30 nM |
| 5-(4-hydroxy-3,5-(bis-N,N-dimethylaminomethyl) benzoyl)-3-thiophene sulfonamide | 155 nM |
| 5-(hydroxymethylbenzoyl)-3-thiophene sulfonamide | 17 nM |
| 5-(4-propionoxybenzoyl)-3-thiophene sulfonamide | 9 nM |
| 5-(3-hydroxybenzoyl)-3-thiophene sulfonamide | 6.7 nM |
| 5-(3-carboxybenzoyl)-3-thiophene sulfonamide | 11, 14 nM |
| 5-(3-formylbenzoyl)-3-thiophene sulfonamide | 7.3 nM |
| 5-(4-butylbenzoyl)-3-thiophene sulfonamide | 8.7 nM |
| 5-(3-trifluoromethylbenzoyl)-3-thiophene sulfonamide | 8.3 nM |
| 5-(2-N,N-dimethylamino-1-ethoxy)carbonylbenzoyl)-3-thiophene sulfonamide | 25 nM |
| 5-(3-butoxycarbonylbenzoyl)-3-thiophene sulfonamide | 25 nM |
| 5-(4-acetoxybenzoyl)-3-thiophene sulfonamide | 3.6 nM |
| [5-(3-sulfonamidothienyl)][2-pyridyl] ketone | 19 nM |
| 5-(4-ethoxycarbonylbenzoyl)-3-thiophene sulfonamide | 6 nM |
| 5-(4-t-butoxycarbonylbenzoyl)-3-thiophene sulfonamide | 3 nM |
| 5-(3-benzoxybenzoyl)-3-thiophene sulfonamide | 5.3 nM |
| 5-(4-formylbenzoyl)-3-thiophene sulfonamide | 13 nM |
| 5-benzoyl-3-thiophene sulfonamide | 13 nM |
| 5-(4-methoxybenzoyl)-3-thiophene sulfonamide | 26 nM |
| 5-(1-heptanoyl)-3-thiophene sulfonamide | 14 nM |
| 5-(1-pentanoyl)-3-thiophene sulfonamide | 27 nM |
| 5-(4-carboxybenzoyl)-3-thiophene sulfonamide | 3.4, 5 nM |
| 5-(4-hydroxybenzoyl)-3-thiophene sulfonamide | 17 nM |
| 5-(4-acetoxymethylbenzoyl)-3-thiophene sulfonamide | 6 nM |
| 5-(2-fluorobenzoyl)-3-thiophene sulfonamide | 18 nM |
| 5-(3-fluorobenzoyl)-3-thiophene sulfonamide | 12 nM |
| 5-(3,5-difluorobenzoyl)-3-thiophene sulfonamide | 15 nM |
| 5-(1-hydroxypentyl)-3-thiophene sulfonamide | 32 nM |
| 5-(4-hydroxymethylbenzhydrol)-3-thiophene sulfonamide | 41 nM |
| 5-(4-formylbenzhydrol)-3-thiophene sulfonamide | 18 nM |
| 5-(1-hydroxyheptanyl)-3-thiophene sulfonamide | 31 nM |
| 5-(4-methoxybenzhydrol)-3-thiophene sulfonamide | 16 nM |
| 5-benzhydrol-3-thiophene sulfonamide | 74 nM |
| 5-(4-acetoxymethylbenzhydrol)-3-thiophene sulfonamide | 21 nM |
| 5-(4-hydroxybenzhydrol)-3-thiophene sulfonamide | 26 nM |
| 5-(3-hydroxybenzhydrol)-3-thiophene sulfonamide | 37 nM |
| 5-[(hydroxy)(pyridyl)methyl]-3-thiophene sulfonamide | 240 nM |
| 5-(acetoxyphenylmethyl)-3-thiophene sulfonamide | 90 nM |
| 5-(4-methoxybenzoyl)-3-thiophene sulfonamide, oxime | 31 nM |
| 5-heptyl-3-thiophene sulfonamide | 21 nM |
| 5-(1-pentanoyl)-3-thiophene sulfonamide, oxime | 22 nM |
| 5-[(methoxy)(4-hydroxymethylphenyl)]methyl-3-thiophene sulfonamide | 13 nM |
| 5-[(methoxy)(3-trifluoromethylphenyl)methyl]-3-thiophene sulfonamide | 18 nM |
| 5-benzoyl-3-thiophene sulfonamide, oxime | 53 nM |

While particular embodiments of the invention have been described it will be understood of course that the invention is not limited thereto since many obvious modifications can be made and it is intended to include within this invention any such modifications as will fall within the scope of the appended claims.

Having now described the invention, what is claimed is:

1. Compounds represented by the structural formula:

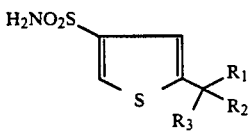

wherein $R_1$ and $R_2$ are independently
   (a) hydrogen
   (b) $OR_4$, wherein $R_4$ is hydrogen or $C_{1-7}$ alkyl or $C_{1-3}$ alkylcarbonyl or phenylcarbonyl or phenyl; or
   (c) $NR_5R_6$, wherein $R_5$ and $R_6$ are independently hydrogen, or $C_{1-7}$ alkyl, or $C_{1-7}$ alkyl substituted with one or more halogen or $OR_4$; or
   (d) —$COR_7$, wherein $R_7$ is hydrogen, $C_{1-7}$ alkyl, or $NR_5R_6$; or
   (e) —$SR_8$, wherein $R_8$ is hydrogen, or $C_{1-7}$ alkyl, or $C_{1-7}$ alkyl substituted with one or more halogen or $OR_4$; or
   (f) $C_{1-7}$ alkyl, or $C_{1-7}$ alkyl substituted with one or more halogen or $OR_4$ or $NR_5R_6$; or
   (g) $R_1$ and $R_2$ are together
      (i) =O, or
      (ii) =$NOR_8$, or
      (iii) =S;
and $R_3$ is
   (h) $C_{1-7}$ alkyl, or $C_{1-7}$ alkyl substituted with one or more halogen or $OR_4$ or $NR_5R_6$; or
   (i) aryl, wherein said aryl comprises up to 10 carbon atoms and is an unsubstituted carbocyclic aryl or heterocyclic aryl radical, or said carbocyclic aryl or heterocyclic aryl radical is substituted with one or more halogen, or $OR_4$ or $NR_5R_6$, or carboxylic acid or lower alkyl esters thereof, or carboxaldehyde or $C_{1-7}$ alkyl, or $C_{1-7}$ alkyl substituted with one or more halogen or $OR_4$ or $NR_5R_6$, or carboxylic acid or lower alkyl esters thereof; or
   (j) —$COR_9$, wherein $R_9$ is $R_7$ or an unsubstituted carbocyclic or heterocyclic radical, wherein said unsubstituted carbocyclic or heterocyclic radical comprises up to 10 carbon atoms, or said carbocyclic or heterocyclic radical is substituted with one or more halogen, or $OR_4$ or $NR_5R_6$, or $C_{1-7}$ alkyl, or $C_{1-7}$ alkyl substituted with one or more halogen or $OR_4$ or $NR_5R_6$.

2. The compound of claim 1 wherein R1 and R2, together, represent O or at least one of R1 or R2 is hydrogen and the other is selected from the group consisting of hydroxy, acetoxy, oxime and hydrogen.

3. The compound of claim 2 wherein $R_3$ is $C_1$ to $C_6$ alkyl or phenyl or phenyl substituted with at least one hydroxy, methoxy, acetoxy, acetoxymethylene, carboxy, hydroxymethyl, formyl, N,N-dimethylaminomethyl, fluoro, chloro or bromo radicals.

4. The compound of claim 3 wherein $R_1$ and $R_2$, together, are oxygen and $R_3$ is phenyl.

5. The compound of claim 3 wherein $R_1$ and $R_2$, together, are oxygen and $R_3$ is p-methoxyphenyl.

6. The compound of claim 3 wherein $R_1$ and $R_2$, together, are oxygen and $R_3$ is hydroxyphenyl.

7. The compound of claim 3 wherein $R_1$ and $R_2$, together, are oxygen and $R_3$ is p-acetoxyphenyl.

8. The compound of claim 3 wherein $R_1$ and $R_2$, together, are oxygen and $R_3$ is p-acetoxymethylphenyl.

9. The compound of claim 3 wherein $R_1$ and $R_2$, together, are oxygen and $R_3$ is p-carboxylic phenyl.

10. The compound of claim 3 wherein $R_1$ and $R_2$, together, are oxygen and $R_3$ is n-butyl.

11. The compound of claim 3 wherein $R_1$ and $R_2$, together, are oxygen and $R_3$ is n-hexyl.

12. The compound of claim 3 wherein $R_1$ is hydrogen, $R_2$ is hydroxy and $R_3$ is phenyl.

13. The compound of claim 3 wherein $R_1$ is hydrogen, $R_2$ is hydroxy and $R_3$ is p-methoxyphenyl.

14. The compound of claim 3 wherein $R_1$ is hydrogen, $R_2$ is hydroxy and $R_3$ is p-hydroxyphenyl.

15. The compound of claim 3 wherein $R_1$ is hydrogen, $R_2$ is hydroxy and $R_3$ is p-acetoxyphenyl.

16. The compound of claim 3 wherein $R_1$ is hydrogen, $R_2$ is hydroxy and $R_3$ is p-acetoxymethylphenyl.

17. The compound of claim 3 wherein $R_1$ is hydrogen, $R_2$ is hydroxy and $R_3$ is p-carboxylic phenyl.

18. The compound of claim 3 wherein $R_1$ is hydrogen, $R_2$ is hydroxy and $R_3$ is n-butyl.

19. The compound of claim 3 wherein $R_1$ is hydrogen, $R_2$ is hydroxy and $R_3$ is n-hexyl.

20. The compound of claim 3 wherein $R_1$ is hydrogen, $R_2$ is hydroxy and $R_3$ is p-formylphenyl.

21. The compound of claim 3 wherein $R_1$ is hydrogen, $R_2$ is hydroxy and $R_3$ is 4-hydroxy-3-N,N-dimethylamiomethylphenyl.

22. The compound of claim 3 wherein $R_1$ is hydrogen, $R_2$ is acetoxy and $R_3$ is phenyl.

23. The compound of claim 3 wherein $R_1$ and $R_2$, together, are oxime and $R_3$ is butyl.

24. The compound of claim 3 wherein $R_1$ and $R_2$, together, are oxime and $R_3$ is p-methoxyphenyl.

25. The compound of claim 2 wherein $R_1$ and $R_2$ are hydrogen and $R_3$ is n-butyl.

26. The compound of claim 1 wherein $R_3$ is aryl.

27. The compound of claim 26 wherein $R_3$ is selected from the group consisting of phenyl, thienyl, furyl, pyridyl, pyrryl, piperidyl, pyrrolidyl and morpholinyl.

28. The compound of claim 1 wherein $R_3$ is -$COR_9$.

29. The compound of claim 28 wherein $R_9$ is aryl.

30. The compound of claim 28 wherein $R_9$ is selected from the group consisting of phenyl, cyclopentyl, cyclohexyl, thienyl, furyl, pyridyl, pyrryl, piperidyl, pyrrolidyl, morpholinyl.

31. A method of treating the elevated intraocular pressure of a patient which comprises administering to said patient an effective amount of a compound according to claim 1.

32. The method of claim 31 which comprises topically administering said compound of claim 1.

33. A method of treating the elevated intraocular pressure of glaucoma in a patient which comprises administering to said patient an effective amount of a compound according to claim 1.

34. The method of claim 33 which comprises topically administering said compound of claim 1.

35. The method of claim 34 which comprises administering a unit dosage of from 0.001 to 10.0 mg of the compound of claim 1 on a daily basis.

36. A pharmaceutical composition for treating a patient having glaucoma, by topical administration, which comprises an effective amount of a compound according to claim 1 in a pharmaceutically-acceptable carrier.

37. The composition of claim 36 comprising from 0.01 to 15% of said compound of claim 1.

38. A method of inhibiting carbonic anhydrase activity in a patient which comprises administering to said patient an effective amount of a compound according to claim 1.

39. The method of claim 31 which comprises topically administering said compound of claim 1.

40. The method of claim 39 which comprises administering a unit dosage of from 0.001 to 10.0 mg of the compound of claim 1 on a daily basis.

* * * * *